United States Patent [19]

Martin et al.

[11] Patent Number: 5,936,129
[45] Date of Patent: Aug. 10, 1999

[54] PROCESS FOR MAKING STERICALLY-HINDERED β-DIKETONES

[75] Inventors: Kevin V. Martin, Greenville, N.C.; Phillip L. Mattison, North Wales, Pa.; Michael J. Virnig, Tucson, Ariz.

[73] Assignee: Henkel Corporation, Plymouth Meeting, Pa.

[21] Appl. No.: 09/010,953

[22] Filed: Jan. 22, 1998

Related U.S. Application Data

[60] Provisional application No. 60/038,916, Feb. 21, 1997.

[51] Int. Cl.$^6$ ...................................................... C07C 45/00
[52] U.S. Cl. ......................... 568/383; 568/314; 568/315; 568/388; 568/382
[58] Field of Search ..................................... 568/314, 391, 568/346, 388, 383, 335, 315, 319, 382

[56] References Cited

U.S. PATENT DOCUMENTS

| | | | |
|---|---|---|---|
| 2,727,818 | 12/1955 | Kenny et al. | |
| 3,742,062 | 6/1973 | Chappelow, Jr. et al. | 260/592 |
| 4,022,866 | 5/1977 | Kuhn et al. | 423/26 |
| 4,065,502 | 12/1977 | MayKay et al. | 260/590 |
| 4,175,012 | 11/1979 | MacKay et al. | 204/108 |
| 4,297,515 | 10/1981 | Eidenschink et al. | 568/331 |
| 4,324,676 | 4/1982 | Gilbert | 568/412 |
| 4,350,661 | 9/1982 | Davis et al. | 422/98 |
| 4,563,256 | 1/1986 | Sudderth et al. | 204/108 |
| 5,015,777 | 5/1991 | Chisolm et al. | 568/314 |
| 5,371,296 | 12/1994 | Yamaguchi et al. | 568/335 |
| 5,457,236 | 10/1995 | Krbechek et al. | 586/314 |
| 5,475,145 | 12/1995 | Chassaing et al. | 568/412 |
| 5,545,762 | 8/1996 | Muhr | 568/346 |

FOREIGN PATENT DOCUMENTS 2414492  6/1992  Australia .

OTHER PUBLICATIONS

"Physical and Chemical Separations svia the Arbiter Process", Kuhn & Arbiter, international Mining Congress, Apr., 1975, Cagliari, italy, pp. 831–847.

"Anaconda's Arbiter Process for Copper", Kuhn & Arbiter, CIM Bulletin, Feb., 1974.

*Primary Examiner*—Shailendra Kumar
*Assistant Examiner*—Sreeni Padmanabhan
*Attorney, Agent, or Firm*—Ernest G. Szoke; Wayne C. Jaeschke; Henry E. Millson

[57] ABSTRACT

A process for making a sterically-hindered beta-diketone involving: (a) providing a solution comprising: (i) an ester; (ii) a base; and (iii) a solvent; (b) adding a ketone selected from the group consisting of an aromatic ketone and a hindered aliphatic ketone, to the solution, to form a condensation reaction mixture, whereby either the ester or the ketone is hindered; (c) reacting the solution with the ketone to form a sterically-hindered beta-diketone; and (d) recovering the sterically-hindered beta-diketone from the condensation reaction mixture.

26 Claims, No Drawings

PROCESS FOR MAKING STERICALLY-HINDERED β-DIKETONES

CROSS-REFERENCE TO RELATED APPLICATIONS

This application claims priority from U.S. provisional application No. 60/038,916, filed Feb. 21, 1997, the disclosure of which is incorporated herein by reference.

FIELD OF THE INVENTION

The present invention generally relates to a process for making sterically-hindered beta-diketones. More particularly, the present invention relates to the production of good yields of sterically-hindered beta-diketones without unwanted by-product production.

BACKGROUND OF THE INVENTION

Liquid ion exchange recovery of metal values from aqueous solutions is rapidly reaching extensive commercial acceptance. Such processing has been described as being deceptively simple since all that is really happening is the transfer of a metal value from Phase A (aqueous) to Phase B (organic) and thence from Phase B to Phase C (aqueous). However, complexities of liquid ion exchange arise in a number of areas including (1) synthesis and manufacture of the reagent system, (2) evaluation of the system's capabilities, and (3) engineering application leading to large scale metal recovery.

The key to a successful application of liquid ion exchange is the reagent. In this respect, the reagent should meet a number of criteria. In the first instance, the reagent must complex with or react with a metal or group of metals. It is also desirable that the reagent shows preference for a single metal where the aqueous starting solutions contain a number of metal values. The reagent should also desirably complex or react to a high degree of completion with the metal under the extraction conditions. Additionally, the reagent, as well as the resulting metal complex, must exhibit satisfactory solubility in practical solvents. Further, the reagent-metal reaction must be reversible so that the metal can be stripped. For economic reasons, the reagent must be acceptably stable so that it can be recycled repeatedly. Also, it should be essentially water insoluble to prevent significant loss into the aqueous phase. Furthermore, the reagent should not cause or stabilize emulsions. And, of course, the cost of the reagent should be such that the liquid ion exchange process can be operated at a profit.

A few compounds have found significant commercial acceptance. U.S. Pat. No. 4,563,256 describes a solvent extraction process for the recovery of zinc values from ammoniacal solutions, which may also contain copper values, using or employing various oxime extractants.

U.S. Pat. No. 2,727,818 describes a method of leaching copper sulfide materials with ammoniacal leach solutions. No solvent extraction is discussed.

U.S. Pat. Nos. 4,065,502 and 4,175,012 describes beta-diketones which may be employed as metal extractants in a liquid-liquid ion exchange process for recovery of metals, such as nickel or copper, from aqueous solutions containing the metal values, including aqueous ammoniacal solutions.

U.S. Pat. No. 4,350,661 describes the extraction of copper from ammoniacal aqueous solutions by a process of extraction first with a beta-diketone followed by a second extraction with an oxime. Alternatively, there is described the use of a mixture of diketone and oxime wherein the extractant reagent comprises about 5–30 percent by volume of the strong reagent (oxime) and 10–60 percent by volume of the weak reagent (beta diketone).

In commonly assigned, co-pending application, U.S. Ser. No. 08/780,759, the entire disclosure of which is hereby incorporated by reference, there is described a sterically-hindered beta-diketone which, due to the steric hindrance around the beta-diketone functionality results in more stability to use conditions, minimizing, if not eliminating, ketimine formation.

While these sterically-hindered beta-diketones appear to be highly effective metal extractants, their production in economically acceptable yields, in the absence of unwanted by-product formation, remains a problem. The utilization of known production techniques results in either low yields and/or the formation of unwanted by-products such as dypnone, which are very difficult to separate from the sterically-hindered beta-diketone product.

SUMMARY OF THE INVENTION

The present invention is directed to a process for making sterically-hindered beta-diketones involving:

(a) providing a solution, at an elevated temperature, containing:
  (i) an ester selected from the group consisting of an aromatic ester and a hindered ester;
  (ii) a strong base; and
  (iii) a solvent;
(b) adding a ketone selected from the group consisting of an aromatic ketone and a hindered aliphatic ketone, to the solution, to form a condensation reaction mixture, wherein either the ester or the ketone is hindered;
(c) reacting the solution with the ketone to form a sterically-hindered beta-diketone; and
(d) recovering the sterically-hindered beta-diketone from the condensation reaction mixture.

DESCRIPTION OF THE INVENTION

In this description, except in the operating examples or where explicitly otherwise indicated, all numbers describing amounts of ingredients or reaction conditions are to be understood as modified by the word "about".

The present invention relates to a process for making sterically-hindered beta-diketones for use in the recovery of metals. While the sterically-hindered beta-diketones produced by the process of the present invention are particularly useful in applications where ammoniacal leach solutions are encountered in the treatment of copper containing sulfidic ores, they may also be applicable or useful in the extraction of copper from any aqueous ammoniacal solution containing copper values regardless of its source.

Since a preferred product of interest in the present invention is 4-ethyl-1-phenyl-1,3-octadione, the invention will be described with respect to the production of this particular product. However, it should be understood that the process of the invention is also applicable to the preparation of other sterically-hindered beta-diketones such as, for example, 1-phenyl-3-neoalkyl-1,3-propanediones, in which the first carbon in the neoalkyl group is fully substituted. A particularly preferred sterically-hindered beta-diketone is 1-phenyl-3-neononyl-1,3-propanedione.

In general, the overall process to produce the sterically-hindered beta-diketone involves: (a) the addition of a ketone to a reaction vessel containing an agitated, heated, mixture of an ester, a strong base, and an organic solvent, (b)

completion of the reaction at an elevated temperature, and (c) recovery of the resultant sterically-hindered beta-diketone product by conventional means.

Recovery of the sterically-hindered beta-diketone from the condensation reaction mixture may include the additional steps of: (d) cooling the reaction mixture, (e) acidifying the resultant reaction product, (f) washing the resultant organic phase containing the sterically-hindered beta-diketone, and (g) purifying the sterically-hindered beta-diketone by distillation.

The primary starting materials in the process of the present invention are the ester and ketone compounds. Both the ester component and the ketone component may be either hindered or aromatic. It is imperative to note, however, that when carrying out the process of the present invention, either the ester or the ketone starting material must be hindered. In a preferred embodiment of the present invention, it is the ester component that is hindered.

Hindered esters which may be used in accordance with the present invention are represented by formula I:

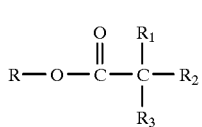
(I)

wherein $R_1$, $R_2$, and $R_3$ may be the same or different, $R_1$ and $R_2$ are alkyl groups containing from 1 to about 8 carbon atoms, $R_3$ is hydrogen or an alkyl group containing from 1 to about 8 carbon atoms, and R is an alkyl group containing 1–4 carbon atoms. Suitable examples thereof include methyl 2-ethylhexanoate, methyl neoheptanoate, methyl neooctanoate, methyl neononanoate, and methyl neodecanoate. The neo prefix means that the carbon next to the carbonyl carbon is completely substituted. Generally, neoalkyl groups are a mixture of isomers. A particularly preferred hindered ester is methyl neodecanoate.

Aromatic methyl ketones which may be employed in the process of the present invention may be generally represented by formula (II):

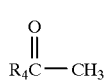
(II)

wherein $R_4$ is phenyl or C1–C15 alkyl substituted phenyl. A particularly preferred ketone is acetophenone.

According to another embodiment of the present invention, the sterically-hindered beta-diketones may also be produced by employing an aromatic ester component in combination with a hindered aliphatic ketone.

Aromatic esters which may be employed in the process of the present invention are those corresponding to formula III:

$$R_5CO_2R_6 \quad (III),$$

wherein $R_5$ is phenyl or $C_1$–$C_{15}$ alkyl substituted phenyl, and $R_6$ is an alkyl group containing from 1 to 10 carbon atoms. Examples of suitable aromatic esters include, but are not limited to, methyl benzoate, methyl 4-isopropylbenzoate, and methyl 4-tert-butylbenzoate.

Hindered aliphatic methyl ketones which may be employed in the process of the present invention are those corresponding to formula IV:

wherein $R_7$, $R_8$ and $R_9$ may be the same or different, $R_8$ may be an alkyl group containing from 1 to about 8 carbon atoms, and $R_9$ and $R_{10}$ may be hydrogen or an alkyl group containing from 1 to about 8 carbon atoms.

Examples of suitable hindered aliphatic methyl ketones include, but are not limited to, pinacolone, methyl isobutyl ketone, and methyl isopentyl ketone.

The amount of ester employed by the process of the present invention can range from about 1.1 to about 10 moles of ester, per mole of ketone, preferably from about 1.5 to about 5 moles of ester, per mole of ketone, and most preferably from about 2 to about 4 moles of ester, per mole of ketone. It should be noted, however, that the above-disclosed mole ratios are not dependent on whether the ester or ketone is chosen as the hindered starting material.

Strong bases which may be employed in accordance with the present invention are those whose conjugate acids have a pKa in water greater than about 20, and preferably greater than about 30. Examples thereof include sodium amide, potassium amide, sodium acetylide, potassium acetylide, and alkali or alkaline earth hydrides including sodium hydride, potassium hydride and calcium hydride. Alkali and alkaline earth hydrides are preferred, with sodium hydride being particularly preferred.

The amount of strong base to be used can range from about 1.8 to about 4 moles of a strong base per mole of hindered ketone, and preferably from about 2.0 to about 3.0 moles of a strong base per mole of hindered ketone, and most preferably about 2.2 moles of a strong base per mole of ketone.

Solvents which may be employed in the present invention generally include aprotic solvents which are inert to strong bases such as sodium hydride. To allow the reaction to reach suitable elevated temperatures, the boiling point of the solvent should be greater than 100° C. Acceptable solvents include ethers such as dibutyl ether and diglyme, hydrocarbon solvents and, preferably, aromatic hydrocarbon solvents. Examples thereof include, but are not limited to, xylene, toluene, cumene and ethylbenzene.

The amount of solvent which may be used can range from about 0.5 to about 10 moles of solvent per mole of ketone, preferably from about 0.75 to about 4.0 moles of solvent per mole of ketone, and most preferably from about 1 to about 3 moles of solvent per mole of ketone.

The present invention is directed to a process for making sterically-hindered beta-diketones, involving providing a solution containing: (i) from about 1.1 to about 10.0 moles, preferably from about 1.5 to about 5.0 moles, and most preferably from about 2.0 to about 4.0 moles of a hindered ester, per mole of ketone, preferably methyl neodecanoate, (ii) from about 1.5 to about 4.0 moles, and preferably about 2 moles, of a strong base, per mole of ketone, preferably sodium hydride, and (iii) from about 0.5 to about 10 moles, preferably from about 0.75 to about 5 moles, and most preferably about 2 moles of an organic solvent, preferably xylene, per mole of ketone. The ester, strong base, and solvent are agitated in the reaction vessel, preferably by stirring, at a temperature ranging from about 100 to about 200° C., preferably from about 110 to about 180° C., and most preferably at the reflux temperature of the organic solvent. To the reaction vessel there is then added a ketone, preferably acetophenone which, optionally, may be diluted with a portion of the above-disclosed organic solvent. The ketone is added to the reaction vessel for a period of time ranging from about 0.5 hr to about 4 hr. The minimum time is that in which the resulting hydrogen gas can be safely vented from the reaction. Once the ketone is added, the condensation reaction may, if desired, be continued at an elevated temperature, preferably at reflux temperature, for a period of time of up to about 4 hours, and preferably from about 0.5 to 2 hours.

Once the condensation reaction is complete, the sterically-hindered beta-diketone is recovered from the reaction mixture by conventional means. Typically, the reaction mixture is then cooled to a temperature of from about 20 to about 60°. The excess strong base is quenched, preferably by adding a material having a weakly acidic proton to allow sufficient control over the generation of hydrogen gas. The reaction mixture is then acidified by adding thereto from about 50 to about 500 g/l, and preferably from about 100 to about 200 g/l of an aqueous acid, preferably sulfuric acid, to a pH of less than 7, and preferably less than 1. The resultant acidified organic phase is then washed with water to remove salts and excess acid. The resultant organic phase is then stripped of volatiles. The residue is then purified by distillation under a reduced pressure, typically from about 0.1 to about 2 torr. The resultant product is a sterically-hindered beta-diketone. The sterically-hindered beta-diketone formed according to the process of the invention contains less than 5%, preferably less than 3%, and most preferably less than 1% by weight of unwanted by-products such as dypnone. Moreover, the amount of sterically-hindered beta-diketone yielded by the process of the present invention should be no less than about 30%, and preferably no less than about 50%.

It should be noted that the process steps are the same regardless of whether the ester starting material or ketone starting material is hindered.

The present invention will be better understood from the examples which follow, all of which are meant to be illustrative only and are not meant to unduly limit the invention in any way.

EXAMPLES

Example 1

A 5000 mL 4 neck round bottom flask equipped with mechanical stirring, a nitrogen inlet, a thermometer, a condenser, and an addition funnel was charged with 60% sodium hydride in mineral oil (202 g, 5.03 mol, 2.0 mol/mol acetophenone), methyl 2-ethylhexanoate (811 g, 5.13 mol, 2.0 mol/mol acetophenone), and xylene (446 g). The mixture was heated to reflux (135° C.), and then a solution of acetophenone (314 g, 2.61 mol) in xylene (186 g) was added over 2 h. The mixture was kept at reflux for an additional 1 h. After cooling to room temperature, the reaction was quenched by the careful addition of methanol (200 mL), and then acidified with 150 g/L sulfuric acid (1800 mL). The mixture was worked up as in Example 1 to yield a product containing 4-ethyl-1-phenyl-1,3-octadione in a crude yield of 90%. Vacuum distillation (150 mtorr) through a 15 cm Vigreux column yielded the product in the heart cut: 4-ethyl-1-phenyl-1,3-octadione (556 g, 97% pure, 2.19 mol; 84% overall yield; bp: 136–164° C.). Dypnone was undetectable in the product.

Example 2

The conditions of Example 1 were repeated except that the following amounts were used: 60% sodium hydride in mineral oil (151 g, 3.78 mol, 1.5 mol/mol acetophenone), methyl 2-ethylhexanoate (826 g, 5.23 mol, 2.0 mol/mol acetophenone), xylene (465 g), and a solution of acetophenone (306 g, 2.55 mol) in xylene (177 g) was added over 2 h. The mixture was kept at reflux for an additional 45 minutes. Workup of the reaction mixture gave material having product in a crude yield of 72%. Vacuum distillation (160 mtorr) through a 15 cm Vigreux column yielded the product in the heart cut: 4-ethyl-1-phenyl-1,3-octadione (415 g, 94% pure, 1.59 mol; 62% overall yield; bp: 143–164° C.). Dypnone was undetectable in the product.

Example 3

The conditions of Example 1 were repeated except that the following amounts were used: 60% sodium hydride in mineral oil (200 g, 5.03 mol. 2.0 mol/mol acetophenone), methyl 2-ethylhexanoate (618 g, 3.91 mol, 1.5 mol/mol acetophenone), xylene (449 g), and then a solution of acetophenone (304 g, 2.53 mol) in xylene (180 g) was added over 1 h. The mixture was kept at reflux for an additional 30 min. Workup of the reaction mixture gave material having product in a crude yield of 89%. Vacuum distillation (200 mtorr) through a 15 cm Vigreux column yielded the product in the heart cut: 4-ethyl-1-phenyl-1,3-octadione (523 g, 97% pure, 2.06 mol; 81% yield; bp: 128–169° C.). Dypnone was undetectable in the product.

Example 4

The conditions of Example 1 were repeated except that the following amounts were used: 60% sodium hydride in mineral oil (100 g, 2.50 mol, 2.0 mol/mol acetophenone), methyl 2-ethylhexanoate (813 g, 5.15 mol, 4.1 mol/mol acetophenone), toluene (231 g), and then a solution of acetophenone (307 g, 2.56 mol) in toluene (180 g) was added over 2 h. The mixture was kept at reflux for an additional 45 min. Workup of the reaction mixture gave material having product in a crude yield of 85%. Vacuum distillation (200 mtorr) through a 15 cm Vigreux column yielded the product in the heart cut: 4-ethyl-1-phenyl-1,3-octadione (264 g, 96% pure, 2.10 mol; 82% overall yield; bp: 128–169° C.). Dypnone was undetectable in the product.

Example 5

The conditions of Example 1 were repeated except that the following amounts were used: 60% sodium hydride in mineral oil (202 g, 5.05 mol, 2.0 mol/mol acetophenone), methyl 2-ethylhexanoate (805 g, 5.09 mol, 2.0 mol/mol acetophenone), toluene (449 g), and then a solution of acetophenone (307 g, 2.56 mol) in toluene (180 g) was added over 4 h. The mixture was kept at reflux for an additional 45 min. Workup of the reaction mixture gave material having product in a crude yield of 90%. Vacuum distillation (200 mtorr) through a 15 cm Vigreux column yielded the product in the heart cut: 4-ethyl-1-phenyl-1,3-octadione (521 g, 96% pure, 2.03 mol; 79% overall yield; bp: 126–164° C.). Dypnone was undetectable in the product.

Example 6

The conditions of Example 1 were repeated except that the following amounts were used: 60% sodium hydride in mineral oil (200 g, 5.03 mol. 2.0 mol/mol acetophenone), methyl 2-ethylhexanoate (801 g, 5.07 mol, 2.0 mol/mol acetophenone), xylene (449 g), and then a solution of acetophenone (304 g, 2.53 mol) in xylene (180 g) was added over 1 h. The mixture was kept at reflux for an additional 90 min. Workup of the reaction mixture gave a material having product in a crude yield of 85%. Vacuum distillation (200 mtorr) through a 15 cm Vigreux column yielded the product in the heart cut: 4-ethyl-1-phenyl-1,3-octadione (523 g, 96% pure, 2.06 mol; 81% overall yield; bp: 135–169° C.). Dypnone was undetectable in the product.

Example 7

The conditions of Example 1 were repeated except that the following amounts were used: 60% sodium hydride in mineral oil (203 g, 5.07 mol, 2.0 mol/mol acetophenone), methyl 2-ethylhexanoate (825 g, 5.22 mol, 2.0 mol/mol acetophenone), xylene (425 g), and then a solution of acetophenone (315 g, 2.62 mol) in xylene (180 g) was added over 2 h. The mixture was kept at reflux for an additional 30 min. Workup of the reaction mixture gave material containing product in a crude yield of 89%. Vacuum distillation (200 mtorr) through a 15 cm Vigreux column yielded the product in the heart cut: 4-ethyl-1-phenyl-1,3-octadione (541 g, 95% pure, 2.09 mol; 80% overall yield; bp: 128–169° C.). Dypnone was undetectable in the product.

Example 8

The conditions of Example 1 were repeated except that the following amounts were used: 60% sodium hydride in mineral oil (200 g, 5.00 mol, 2.0 mol/mol acetophenone), methyl 2-ethylhexanoate (872 g, 5.08 mol, recycled ester recovered from previous examples, 2.0 mol/mol acetophenone), xylene (357 g), and then a solution of acetophenone (303 g, 2.52 mol) in xylene (174 g) was added over 1 h. The mixture was kept at reflux for an additional 30 min. Workup of the reaction mixture gave material containing product in a crude yield of 83%. Vacuum distillation (200 mtorr) through a 15 cm Vigreux column yielded the product in the heart cut: 4-ethyl-1-phenyl-1,3-octadione (504 g, 94% pure, 1.92 mol; 76% overall yield; bp: 131–169° C.). Dypnone was undetectable in the product.

Example 9

Preparation of 1-Phenyl-3-neoheptyl-1,3-propandione

A 500 mL 4 neck round bottom flask equipped with mechanical stirring, a nitrogen inlet, a thermometer, a condenser, and an addition funnel was charged with 60% sodium hydride in mineral oil (20.5 g, 0.51 mol), methyl neo-octanoate (92.3 g, 0.58 mol), and xylene (42.8 g). The mixture was heated to reflux (135° C.), and then a solution of acetophenone (32.4 g, 0.27 mol) in xylene (19.1 g) was added over 1.25 h. The mixture was kept at reflux for an additional 1 h. After cooling to room temperature, the reaction was quenched by the careful addition of methanol (20 mL), and then acidified with 150 g/L sulfuric acid (180 mL). After separation of layers, the organic phase was washed with water (2×100 mL) and brine (100 mL). After drying by passing through anhydrous sodium sulfate, the solution was concentrated in vacuo at 70° C. down to 12 mbar to yield an orange liquid containing product in a crude yield of 63%. Vacuum distillation (200 mtorr) through a 15 cm Vigreux column yielded the product in the heart cut: 1-phenyl-3-neoheptyl-1,3-propanedione (37.2 g, 96% pure, 0.14 mol; 53% yield; bp: 94–135° C.). Dypnone was undetectable in the product.

Example 10

Preparation of Methyl neo-decanoate neo-Decanoic acid (1,376 g, 8.0 mol) and methanol (1,280 g, 40 mol) were placed in a 5-liter four-neck round-bottomed flask equipped with a mechanical stirrer, a condenser and a thermometer. To the mixture at ambient temperature was added conc sulfuric acid (548 g, 5.6 mol) in a dropping funnel for 15 min, raising the pot temp to 55° C. at the end of the addition. The resulting mixture was kept overnight (20–24 h) under reflux with vigorous stirring and then cooled to ambient temperature. The aqueous phase separated, and the remaining organic layer was washed with water until the pH of the last washing was >4. One gram of the organic phase was withdrawn and titrated with 1.0 N NaOH. The calculated amount of NaOH was added to remove the unreacted neo-decanoic acid present in the crude ester. Then the ester was washed with water (88 mL×3) followed by brine (NaCl-saturated, 500 mL). About 100 mL methanol was added into the crude ester and then the resulting mixture was distilled to obtain methyl neodecanoate (749 g, 4.03 mol) at 175–205° C. at atmospheric pressure. The purity of the ester was >99%, and the yield 50% yield.

Example 11

Preparation of 1-Phenyl-3-neononyl-1,3-propanedione

Sodium hydride (200 g, 5 mol, 60% dispersion in mineral oil) was placed in a 5-liter four-neck round-bottomed flask equipped with a mechanical stirrer, a condenser and a thermometer under a nitrogen atmosphere. To the sodium hydride was added xylenes (600 g, 5.65 mol) and methyl neo-decanoate (1163 g, 6.25 mol) in a dropping funnel at ambient temperature, while carefully watching the pot temperature and nitrogen gas flow. The resulting slurry was heated to 150° C. while vigorously stirring (300 rpm or so) under a nitrogen atmosphere, and acetophenone (301 g, 2.5 mol) was introduced in portions over 3h maintaining the same temperature. After completion of the addition, the mixture was stirred an additional 30 min. The mixture was then cooled to ambient temperature, and treated with cold water (100 mL) and then cold aqueous sulfuric acid (2 liter of 125 g $H_2SO_4$ per liter) keeping the temperature below 30° C. After transfer of the solution into a 5-liter separatory funnel, aqueous phase was separated and the remaining organic layer washed with water (800 mL×3) followed by brine (NaCl saturated, 500 mL). Most of low boiling components (mostly xylenes) were removed by a rotary evaporator (80° C. at 10–20 mbar). Distillation using a 15-cm Vigreux distill column in vacuo gave 1-phenyl-3-neononyl-1,3-propanedione (481 g, 1.76 mol) in 61% yield, after combining the fractions distilled at 185–196° C. at 1.5–2 mmHg.

Comparative Example 1

Preparation of 4-ethyl-1-phenyl-1,3-octadione

A 500 mL 4 neck round bottom flask equipped with mechanical stirring, a thermometer, an addition funnel, and a 30 cm Vigreux column with a distillation head was charged with sodium methoxide (14.7 g, 0.27 mol), methyl 2-ethylhexanoate (59.3 g, 0.37 mol), and toluene (46.0 g). The mixture was heated to reflux (90° C.), and then a solution of acetophenone (30.1 g, 0.25 mol) in toluene (25 g) was added over 2 h. Whenever the temperature at the distillation head was greater than 80° C., the liquid was allowed to drain. The mixture was kept at reflux for an additional 0.5 h. The reaction was cooled to room temperature and acidified with 150 g/L sulfuric acid (80 mL). After separation of layers, the organic phase was washed with water (2×100 mL), sat. sodium bicarbonate (100 mL), water (100 mL) and brine (100 mL). After drying by passing through anhydrous sodium sulfate, the solution was concentrated in vacuo at 70° C. down to 12 mbar to yield a yellow liquid (76.4 g). Vacuum distillation (90 mtorr) through a 15 cm Vigreux column gave the product in the heart cut: 4-ethyl-1-phenyl-1,3-octadione (8.02 g, 76% pure, 0.024 mol; 10% yield; bp: 116–120° C.). The heart cut also contained 4% 1,3-diphenyl-2-buten-1-one (aka. dypnone).

Comparative Example 2

A 500 mL 4 neck round bottom flask equipped with mechanical stirring, a nitrogen inlet, a thermometer, a condenser, and an addition funnel was charged with 60% sodium hydride in mineral oil (20.5 g, 0.51 mol), methyl 2-ethylhexanoate (81.1 g, 0.51 mol), and tetrahydrofuran (THF, 150 mL). The mixture was heated to reflux (74° C.), and then a solution of acetophenone (31.0 g, 0.26 mol) in THF (50 mL) was added over 2 h. The mixture was kept at reflux for an additional 1 h. After cooling to room temperature, the reaction was quenched by the careful addition of methanol (20 mL). The mixture was diluted with toluene (100 mL) and acidified with 150 g/L sulfuric acid (170 mL). The mixture was worked up as in Example 1 to yield an orange liquid (101.7 g). Vacuum distillation (90 mtorr) through a 15 cm Vigreux column yielded the following products: 4ethyl-1-phenyl-1,3-octadione (52.3 g, 85% pure, 0.18 mol; 69% yield; bp: 110–152° C.); dypnone (3.8 g, 84% pure, bp: 152–175° C.). The residue (ca. 1 g) has an IR consistent with a polymer of the last product. The 4-ethyl-1-phenyl-1,3-octadione fraction was contaminated with dypnone (10%), and was further purified by passing it through a silica gel column (800 g, eluent: 20% toluene/heptane); the product was isolated as a yellow liquid (42.8 g, 92% pure, 67% overall yield).

Comparative Example 3

A 3000 mL 4 neck round bottom flask equipped with mechanical stirring, a nitrogen inlet, a thermometer, a condenser, and an addition funnel was charged with 60% sodium hydride in mineral oil (118 g, 2.95 mol), methyl 2-ethylhexanoate (440 g, 2.78 mol), and THF (1000 mL). The mixture was heated to reflux (74° C.), and then a solution of acetophenone (182 g, 1.52 mol) in THF (250 mL) was added over 3 h. The mixture was kept at reflux for an additional 1.5 h. After cooling to room temperature, the reaction was quenched by the careful addition of methanol (125 mL). The mixture was diluted with toluene (500 mL) and acidified with 150 g/L sulfuric acid (1000 mL). The mixture was worked up as in Example 1 to yield an orange liquid (594.4 g). Vacuum distillation (100 mtorr) through a 15 cm Vigreux column yielded the following products: 4-ethyl-1-phenyl-1,3-octadione (259.7 g, 77% pure, 0.82 mol; 54% yield; bp: 126–172° C.); dypnone (26.7 g, 79% pure, bp: 174–215° C.). The residue (ca. 10 g) has an IR consistent with a polymer of dypnone. The 4-ethyl-1-phenyl-1,3-octadione was contaminated with dypnone (15%).

Comparative Example 4

A round bottom flask equipped with mechanical stirring, a nitrogen inlet, a thermometer, and an addition funnel was charged with 60% sodium hydride in mineral oil (50 g, 1.24 mol), THF (500 mL), and methyl neodecanoate (229 g, 1.23 mol), and the mixture was stirred at room temperature. Acetophenone (74 g, 0.62 mol) was added over 45 min. The temperature was slowly raised to 60° C. and maintained at that temperature for 24 hr. A sample was withdrawn, and analysis indicated the reaction was perhaps ¼ complete. The reaction mixture was stirred at 60° C. for a total of eight days, continuously and slowly evolving hydrogen gas. Methanol was added to quench excess sodium hydride, followed by dilute sulfuric acid. The separated organic phase was washed with water, and volatiles were removed under vacuum. The residue was diluted with heptane and washed with 10% potassium hydroxide, then with water, and the volatiles removed under vacuum to leave 267 g. This was distilled, giving a heart cut at about 130° C. at a pressure of 0.1 mm Hg. Thin layer chromatography indicated the presence of some acetophenone plus two major components of similar size. The heart cut was purified by flash chromatography. Heptane elution provided 48 g of the less polar component, which was distilled at 165° C. at 1 mm Hg to give 44 g (0.16 mol, 26% yield) of 1-phenyl-3-neononyl-1,3-propanedione. Toluene elution provided 21 g of the more polar component, which was shown to be dypnone.

As can be seen from the results obtained above, the process of the present invention, namely, Examples 1–9, produces greater yields of the desired sterically-hindered beta-diketone, and small amounts of unwanted by-product.

What is claimed is:

1. A process for making a sterically-hindered beta-diketone comprising:
   (a) providing a solution comprising:
      (i) a hindered aliphatic ester of formula I

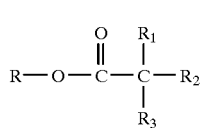

(I)

wherein $R_1$, $R_2$, and $R_3$ may be the same or different, $R_1$ and $R_2$ are alkyl groups containing from 1 to about 8 carbon atoms, $R_3$ is hydrogen or an alkyl group containing from 1 to about 8 carbon atoms, and R is an alkyl group containing 1–4 carbon atoms;
      (ii) a strong base; and
      (iii) a solvent having a boiling point greater than 100° C.;
   (b) adding a ketone selected from the group consisting of an aromatic methyl ketone and hindered aliphatic methyl ketone, to the solution, to form a condensation reaction mixture;
   (c) reacting the solution with the ketone to form a sterically-hindered beta-diketone; and
   (d) recovering the sterically-hindered beta-diketone from the condensation reaction mixture.

2. The process of claim 1 wherein the hindered ester in step (a) is methyl neodecanoate.

3. The process of claim 1 wherein the ketone is a hindered aliphatic methyl ketone.

4. The process of claim 1 wherein in step (b) the ketone is an aromatic methyl ketone.

5. The process of claim 4 wherein the aromatic methyl ketone is acetophenone.

6. The process of claim 1 wherein the ester and ketone are reacted at a mole ratio ranging from about 1.1:1 to about 10:1.

7. The process of claim 6 wherein the ester and ketone are reacted at a mole ratio of from about 2:1 to about 4:1.

8. The process of claim 1 wherein the base is a strong base having a conjugate acid with a pKa greater than 20.

9. The process of claim 1 wherein the base and ketone are employed at a mole ratio ranging from about 1.8:1 to about 4.0:1.

10. The process of claim 9 wherein the base and ketone are employed at a mole ratio of from about 2:1 to about 3:1.

11. The process of claim 1 wherein the solvent and ketone are employed at a mole ratio ranging from about 0.5:1 to about 10:1.

12. The process of claim 11 wherein the solvent and ketone are employed at a mole ratio of about 2:1.

13. The process of claim 1 wherein step (c) is conducted under agitation and at a temperature ranging from about 110 to about 180° C.

14. The process of claim 1 wherein the solution is heated to a temperature of from about 100 to about 200° C., prior to addition of the ketone to the solution.

15. A process for making sterically-hindered beta-diketones comprising:
   (a) providing a solution comprising:
      (i) 2 moles of an ester component consisting of methyl neodecanoate, per mole of ketone;
      (ii) 2 moles of a strong base component consisting of sodium hydride, per mole of ketone; and
      (iii) 1 mole of an organic solvent component, per mole of ketone, wherein the solution is agitated and has a temperature ranging from about 110 to about 140° C.;
   (b) adding a ketone consisting of acetophenone, to the solution, to form a condensation reaction mixture;
   (c) agitating the condensation reaction mixture, at a temperature of from about 110 to about 140° C., for a period of from about 10 to about 90 min.; and
   (d) recovering the sterically-hindered beta-diketone from the condensation reaction mixture.

16. The product of the process of claim 2.

17. The process of claim 1 wherein in step (a) the hindered ester is an ester of formula I in which $R_3$ is an alkyl group.

18. The process of claim 1 wherein in step (a) the hindered ester is methyl neodecanoate, methyl 2-ethylhexanoate, methyl neoheptanoate, methyl neooctanoate, or methyl neononanoate; and wherein the neo prefix means that the carbon atom next to the carbonyl carbon is completely substituted.

19. The process of claim 1 wherein in step (b) the ketone is an aromatic methyl ketone of formula II below

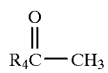

(II)

wherein $R_4$ is phenyl or $C_1$–$C_{15}$ alkyl substituted phenyl.

20. The process of claim 1 wherein in step (b) the hindered aliphatic methyl ketone has the formula IV below

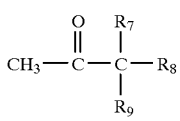

(IV)

wherein $R_7$, $R_8$ and $R_9$ may be the same or different, $R_8$ is an alkyl group containing from 1 to about 8 carbon atoms, and $R_9$ and $R_{10}$ are hydrogen or an alkyl group containing from 1 to about 8 carbon atoms.

21. The process of claim 20 wherein the ketone of formula IV is pinacolone, methyl isobutyl ketone, or methyl isopentyl ketone.

22. The process of claim 1 wherein in step (a) the strong base is sodium amide, potassium amide, sodium acetylide, potassium acetylide, or an alkali or alkaline earth hydride.

23. The product of the process of claim 17.

24. The product of the process of claim 20.

25. The product of the process of claim 21.

26. The product of the process of claim 15.

* * * * *